United States Patent [19]
Titus et al.

[11] Patent Number: 5,650,421
[45] Date of Patent: Jul. 22, 1997

[54] PREMIXED FAMOTIDINE FORMULATION

[75] Inventors: Allan E. Titus, Round Lake; Douglas G. Johnson, Grayslake, both of Ill.

[73] Assignee: Baxter International Inc., Deerfield, Ill.

[21] Appl. No.: 414,433

[22] Filed: Mar. 31, 1995

[51] Int. Cl.$^6$ .................................................. A61K 31/425
[52] U.S. Cl. ................................................. 514/370
[58] Field of Search ................................... 514/370

[56] References Cited

U.S. PATENT DOCUMENTS 4,283,408  8/1981  Hirata et al. ............................ 514/370
4,585,790  4/1986  Padfield et al. .
5,304,571  4/1994  Johnson et al. .
5,364,616  11/1994  Singer et al. ............................ 424/52

OTHER PUBLICATIONS

Johnson & Johnson Mid–Year Report 1995, Cover and p. 11.
*The Merck Index*, Merck & Co., Inc., 1989, p. 617.

*Primary Examiner*—Raymond Henley, III
*Attorney, Agent, or Firm*—Mark Buonaiuto; Monique Morneault

[57] ABSTRACT

A pharmaceutical composition comprising a solution having an effective amount of famotidine, the solution having a pH in the range of about 4.5 to about 8.0, and a shelf life greater than 30 days.

8 Claims, 1 Drawing Sheet

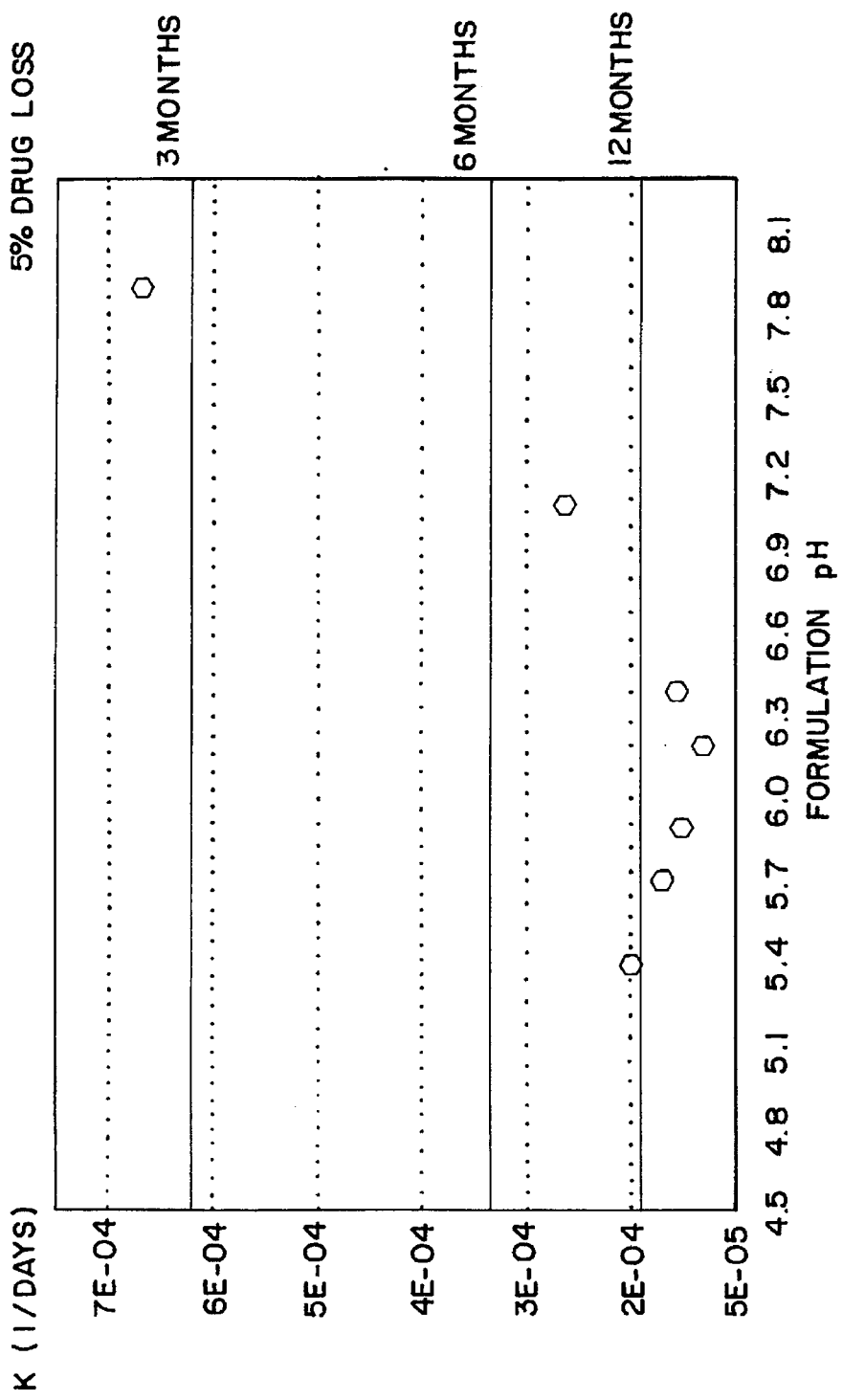

PREMIXED FAMOTIDINE FORMULATION

TECHNICAL FIELD

This invention relates to pharmaceutical compositions, and more specifically to an aqueous-based, premix formulation of famotidine. The aqueous famotidine formulation is suitable for intravenous administration and has an enhanced shelf-life.

BACKGROUND PRIOR ART

Famotidine (N-(aminosulfonyl)-3-[(diaminomethylene)]-4-thiazolyl]methyl]thio]propani midamide), is known commercially as Pepcid®. Famotidine has the ability to inhibit gastric acid secretion through a histamine $H_2$-receptor. Histamine $H_2$-receptor blocking agents have the ability to inhibit the basic secretion of gastric acid and the gastric acid secretion induced by gastrin histamine, methacholine or food. Therefore, these compounds are useful in the treatment of gastric ulcer and duodenal ulcer caused by the hypersecretion of gastric acid.

A process for preparing famotidine, or guanidinothiazole compounds, and medical compositions containing such compounds are described in U.S. Pat. No. 4,283,408, issued Aug. 11, 1981 to Hirata et al., which is incorporated herein by reference.

Famotidine is currently sold in a concentrated form by Merck, Sharpe and Dohme for admixing with a suitable diluent for parenteral administration. To achieve a useful shelf life of the concentrated famotidine solution, which has a pH of 5.3, the solution must be stored at refrigerated temperatures. After mixing, by a pharmacist or other medical personnel, of a suitable aliquot of the concentrated famotidine with the diluent, the shelf life of the admixed solution is limited to not more than 14 days for sterility purposes as required by hospitals and other healthcare providers. Furthermore, the admixed solution must be refrigerated to achieve this shelf life.

The mixing step required by the current famotidine product, the refrigerated storage of the concentrate, as well as its limited shelf life after admixing present several disadvantages. During the preparation of the admixed solution, a possibility exists of dosage miscalculation, as well as contamination of the solution during the mixing step. The refrigeration storage of the admixed solution is an inconvenience and requires special handling. The reduced shelf life and admixing step leads to increased waste disposal as the components required to prepare the admixed solution, such as vials, needles and bags, as well as the unused portion of the concentrated solution, must be properly discarded. All of these disadvantages, including special handling and extra components, contribute to higher costs of the admixed solution. Finally, in cases where needles are used during the mixing step, there is an increased possibility of needle sticks to medical personnel.

The formulations of the present invention overcome the disadvantages of existing famotidine solutions as they are premixed and stable at room temperature, without the need for refrigeration, for long periods of time. In addition, the present formulation avoids any potential problems of contamination, needle sticks, increased waste, and dosage calculation errors as medical personnel can simply pull a prepared bag off the shelf for immediate use.

SUMMARY OF THE INVENTION

New aqueous-based, premix formulations of famotidine and/or one or more of its physiologically acceptable salts, have now been formulated which are suitable for intravenous administration and continuous infusions. These premixed aqueous-based famotidine formulations are extremely stable at room temperature within a specific pH range of 4.5–8.0, allowing for long-term storage and shelf-life well in excess of one month, and in most cases in excess of one year, with not more than 5% drug loss. While the present formulations do not require refrigeration for storage, the shelf life of these formulations can be increased with refrigeration, freezing, or allowing for 10% drug loss.

Other advantages and aspects of the present invention will become apparent upon reading the following detailed description of the invention.

BRIEF DESCRIPTION OF THE FIGURES

FIG. 1 is a pH-rate profile of famotidine solutions.

DETAILED DESCRIPTION

While this invention is susceptible of embodiment in many different forms, this disclosure will describe in detail preferred embodiments of the invention. The present disclosure is to be considered an example of the principles of the invention, and is not intended to limit the broad aspect of the invention to the embodiments illustrated.

In greater detail, the invented formulations offer a number of advantages over other forms of administration of famotidine. For example, the aqueous-based famotidine formulations of the present invention demonstrate long-term stability and enhanced shelf-life when prepared at a physiologically suitable pH range. This stability remains even at room temperature without the requirement of refrigeration needed by prior formulations. In addition, the premixed formulations are less expensive, saving time and effort which may otherwise be required by medical staff in mixing up such formulations for intravenous administration. The premix formulations also avoid the possibility of dosage admixing errors by medical staff.

Famotidine (N-(aminosulfonyl)-3-[(diaminomethylene)]-4-thiazolyl] methyl]thio]propanimidamide) and/or one or more physiologically acceptable salts thereof, are preferred for use in the present invention. Salts of famotidine include compounds with inorganic or organic acids. Example of inorganic acid salts are hydrochlorides, hydrobromides, sulfates, etc. Example of useful organic acid salts include salts with aliphatic carboxylic acids such as acetic acid, maleic acid, fumaric acid, etc. The famotidine used in the present invention was obtained in powder form from Merck, Sharp & Dohme, Pennsylvania. The preferred concentration of famotidine is about 0.1 to about 0.8 mg/ml, more preferably about 0.1 to about 0.4 mg/ml, and most preferably about 0.360 to about 0.440 mg/ml. These amounts allow for an effective dosage of 20 mg–40 mg to be delivered in common dosage amounts of 50–250 ml.

The formulations of the present invention may be prepared by dissolving an appropriate amount of famotidine in a carrier or diluent suitable for intravenous administration to patients. Such carriers include Ringer's lactate, 5% dextrose, 0.45% sodium chloride in water for injection (half normal saline), and preferably 0.9% sodium chloride in water for injection (normal saline).

The formulations of the present invention are prepared by dissolving the preferred amount of famotidine and/or one or more physiologically acceptable salts thereof in water in a suitable mixing device. The pH of the formulation is then adjusted through the addition of any appropriate acid, including amino acids, carboxylic acids, or other acids suitable for pharmaceutical preparations. The preferred acid is L-aspartic acid. The pH of the formulation is determined through the use of a potentiometer per the USP <791>. The amount of amino acid useful in the present invention is preferably 0.14 mg/ml in a 50 ml delivered volume. Preferably, the pH of the formulation should be in the range of about 4.5 to 8.0, and most preferably about 5.7 to about 6.4. These pH ranges are preferred because the formulation is particularly stable, demonstrating a low percent of drug loss over a long period of time. (See FIG. 1). The stability of the formulation, allows for room temperature storage of the solution avoiding the need for extra refrigeration equipment. Enhanced shelf life and reliability are advantages demonstrated by the present formulation over prior formulations as illustrated in Table 1 below.

TABLE 1

| initial pH | real time expiry (5% drug loss) |
|---|---|
| 5.3 | 299 days at 25° C. |
| 5.7 | 429 days at 25° C.* |
| 5.9 | 803 days at 25° C.** |
| 6.0 | 893 days at 25° C. |
| 6.1 | 984 days at 25° C. |
| 6.4 | 485 days at 25° C.* |
| 7.0 | 225 days at 25° C. |
| 8.0 | 48 days at 25° C. |

*- extrapolated from data collected up to 369 days
**- extrapolated from data collected up to 738 days A process for producing the pharmaceutical composition of the present invention comprises the steps of: (a) dissolving an effective amount of famotidine into a suitable liquid forming a solution; (b) adjusting the pH of the solution to a range of about 4.5 to about 8.0; and (c) filling suitable containers with the solution. The process can include the step of sterilizing the solution either before or after the filling step, by any suitable sterilization method including heat, radiation or preferably through filter membrane sterilization.

The present invention is described further by the following examples. These examples are for the purpose of illustration and should not limit the scope of the invention.

EXAMPLE 1

In a tank equipped with a mixer, 9.0 mg/ml of sodium chloride (normal saline) was added to 900 ml water suitable for injection and mixed until dissolved as measured visually. Next, 0.14 mg/ml of aspartic acid was added with agitation until dissolved in about 10 to 15 minutes. Finally, 0.4 mg/ml of famotidine was added with agitation and dissolved. The pH of the solution was measured, as described earlier and adjusted, if necessary, through the further addition of aspartic acid or sodium hydroxide. The solution was brought up to a final volume of 1 liter with water suitable for injection. The solution was then sterilized by filtration through a 0.2 micron membrane filter. Finally, suitable containers, such as Glaxy® infusion containers, were aseptically filled with the solution. The solution can be stored at room temperature, preferably at 25° C., for up to one year or longer with less than 5% drug loss. Famotidine degradation was measured using high-performance liquid chromatography (HPLC).

EXAMPLE 2

Example 2 was prepared according to the procedure described for Example 1 except for the following changes: 0.2 mg/ml famotidine, 0.08 mg/ml aspartic acid and 9.0 mg/ml sodium chloride (normal saline). The pH was adjusted to 7.0 by addition of sodium hydroxide.

EXAMPLE 3

Example 3 was prepared according to the procedure described for Example 1 except for the following changes: 0.2 mg/ml famotidine, 0.08 mg/ml aspartic acid, 50 mg/ml dextrose, hydrous. The pH was adjusted to 6.3 by addition of sodium hydroxide.

We claim:

1. A pharmaceutical composition suitable for administration parenterally and through injection, comprising a solution having an effective amount of famotidine, or at least one physiologically acceptable salt of famotidine, between about 0.1 mg/ml to about 0.8 mg/ml, the solution having a pH adjusted by an acid to be in the range of 5.7 to about 6.4.

2. The pharmaceutical composition of claim 1 wherein the acid includes carboxylic acids and amino acids.

3. The pharmaceutical composition of claim 2 wherein the acid includes L-aspartic acid.

4. A process of making a pharmaceutical composition including famotidine, the composition having a shelf life in excess of 30 days, and is useful in parenteral administration, comprising:

(a) dissolving an effective amount of famotidine or at least one physiologically acceptable salt of famotidine into a suitable liquid forming a premixed solution;

(b) adjusting the pH of the premixed solution using an acid suitable for pharmaceutical preparations to a range of 5.7 to about 6.4; and, (c) filling suitable containers with the premixed solution.

5. The process of claim 4 wherein the steps further include sterilization of the solution by any suitable sterilization method.

6. The process of claim 5 wherein the sterilizing step is by filtration.

7. The process of claim 4 wherein the effective amount of famotidine is between about 0.1 mg/ml to about 0.8 mg/ml.

8. The process of claim 4 wherein the acid suitable for pharmaceutical preparations includes aspartic acid.

* * * * *